United States Patent [19]

Smathers

[11] 4,100,360

[45] Jul. 11, 1978

[54] PROCESS FOR MAKING LOWER ALKYL FORMATES

[75] Inventor: Donald Lee Smathers, Wilmington, Del.

[73] Assignee: E. I. Du Pont de Nemours and Company, Wilmington, Del.

[21] Appl. No.: 772,859

[22] Filed: Feb. 28, 1977

[51] Int. Cl.$^2$ ............................................. C07C 67/36
[52] U.S. Cl. .................................................... 560/232
[58] Field of Search .................... 260/488 K; 560/232

[56] References Cited

U.S. PATENT DOCUMENTS 3,816,513  6/1974  Wakamatsu et al. ............ 260/488 K

*Primary Examiner*—Vivian Garner

[57] ABSTRACT

A process for making lower alkyl formates by contacting an intimate admixture of gaseous CO and liquid lower alkanol with a strongly basic anion exchange resin.

9 Claims, No Drawings

PROCESS FOR MAKING LOWER ALKYL FORMATES

FIELD OF THE INVENTION

The invention relates to an improved process for making lower alkyl formates by the catalytic reaction of lower alkanols with CO. In particular, the invention relates to the use of an heterogeneous catalyst for the process.

BACKGROUND OF THE INVENTION

Methyl formate (MF) is a clear, colorless and volatile liquid having a boiling point of only 31.8° C. It is used as an ingredient in fumigants, as a solvent and as intermediate in the manufacture of numerous organic chemicals and drugs. Though textbooks speak of the esterification of formic acid with methanol to make methyl formate, a more economical and therefore more widely used process involves the reaction of methanol with gaseous carbon monoxide in the presence of a sodium methoxide catalyst dissolved in methanol. Higher alkyl formates are prepared similarly or by transesterification with methyl formate.

BRIEF SUMMARY OF THE INVENTION

It has now been discovered that lower alkyl formates can be made by a process which comprises the steps of contacting an intimate admixture of gaseous CO and liquid lower alkanol with a strongly basic anion exchange resin. In particular, the process is carried out at temperatures of 0°–200° C at a CO partial pressure of 100–5,000 psia.

DETAILED DESCRIPTION OF THE INVENTION

The reaction on which the invention is based is as follows:

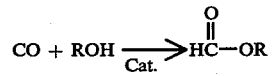

Suitable alkanols are the $C_{1-4}$ alkanols of which methanol is preferred because of higher reactivity and greater ease of separation from the reaction mixture. Any unreacted alkanol is readily removed from the reaction mixture by distillation and can be recycled to the process.

The carbon monoxide for the reaction need not be of especially high purity. Consequently, either rather pure CO or quite dilute CO mixtures such as a synthesis gas can be used in the process since most diluents such as $CO_2$ and $H_2$ will go through the process unchanged. The purity of CO feed is therefore likewise a matter of economics. Obviously, the presence of diluent increases the gas handling and equipment size requirements and will be preferably minimized in most instances. It is preferred that the CO feed to the process be substantially free of $CO_2$ since its presence will reduce catalyst effectiveness. Various pretreatments can, of course, be used to remove the $CO_2$ from CO-containing gas streams containing excess amounts of $CO_2$.

It will ordinarily be preferred to use approximately stoichiometric ratios of CO and alkanol since the amount of unreacted feed materials is minimized thereby. Nevertheless, the mole ratio of reactants is not at all critical and can range from as low as 0.05 to as high as 20 CO/alkanol. It is preferred, however, to operate at a feed mole ratio of CO to alkanol which is from 0.1 to 3.0 and preferably still about 0.5 to 1.5.

In order to obtain better mass transfer and generally more rapid reaction rates, it is preferred to operate the process at CO partial pressure of at least 100 psi. Moreover, useful operating pressures extend to at least about 5000 psia or even higher. However, economically preferred operating pressures are 100–1500 psia CO partial pressure and especially 1000–1500 psia.

The heterogeneous catalyst used in the process of the invention must be a strongly basic anion exchange resin. Typical of such resins is poly(styrene-divinylbenzene), the ion-active portion of which is a quaternary ammonium group. These materials are prepared by chloromethylation of the solid copolymer, usually in bead form, using chloromethyl methyl ether and a Friedel Crafts catalyst such as aluminum chloride, stannic chloride, ferric chloride or zinc chloride:

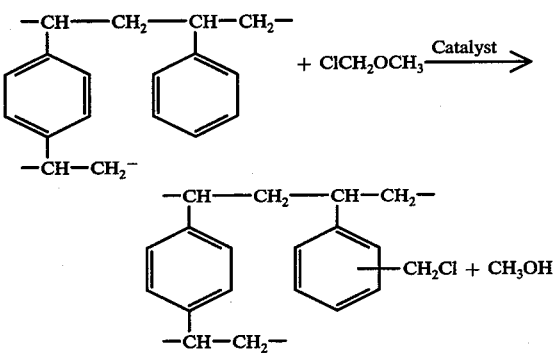

The thusly chloromethylated resin is then reacted with a tertiary amine dissolved in polar solvent to form a quaternary ammonium salt.

An alternative approach is by side chain chlorination of poly(vinyl toluene) to form poly(vinyl benzyl chloride) which is then treated with tertiary amine to form the quaternary ammonium salt.

A variety of tertiary amines can be used to form the ion-active group for the polymer matrix especially those corresponding to the structure $NR_3$ in which the R groups are independently selected from the group consisting of $C_{1-4}$ alkyl and hydroxyl-substituted $C_{1-2}$ alkyl groups. However, those which are most widely available are derived from trimethylamine and dimethylethanolamine. Commercially available resins prepared from the trimethylamine include Amberlite [1] IRA-400, Amberlite IRA-401, Amberlite IRA-402, Amberlite IRA-900, Duolite [2] A-101-D, Duolite ES-111, Dowex[3] 11, Dowex 21K and Ionac [4] A-540. Commercially available resins prepared from dimethylethanolamine include Amberlite IRA-410, Amberlite IRA-911, Dowex 2, Duolite A-102-D, Ionac A-542 and Ionac A-550. Other available quaternary ammonium resins include Amberlyst[1] A-26 and Amberlyst A-27.

[1] Trade name of Rohm & Haas Co., Philadelphia, PA [2] Trade name of Diamond Alkali Co., Redwood City, CA [3] Trade name of The Dow Chemical Co., Midland, MI [4] Trade name of Ionac Chemical Co., Div. of Pfaudler Permutit Inc., Birmingham, NJ.

The above-described ion-exchange resins are available in particulate form as granules or spheres, usually ranging from about 400 mesh (about 40μ) to 16 mesh (1.2 mm) and have a specific gravity in the range of 1.1–1.5. These materials can be used in the process of the invention either as a fixed bed through which the reactants are passed downwardly or the resin can be slurried in the reactants and then separated from the reaction mixture by settling and/or filtration. A continuous moving bed of catalyst may also be used especially when the resin has suitable resistance to attrition.

Because the catalyst is completely insoluble in the reactants and product and is in particulate form, the process can be carried out either batchwise or continuously. When the process is carried out batchwise, the resin catalyst is slurried in the reactants for a time sufficient to assure contact with the resin surface, separated from the reaction mixture by settling and decantation or by filtration of the slurry. Either co-current or counter-current operation of the reactor is feasible. It is preferred, however, to carry out the process continuously by passing the reactants through a fixed bed of resin. A preferred manner of doing this is to pass a downflowing stream of liquid alkanol through a fixed bed of catalyst resin while simultaneously passing downwardly through the bed a finely divided stream of gaseous CO. Any unconverted CO and/or diluent is then passed from the bottom of the contacting vessel for purification or other disposition and liquid formate product dissolved in any unreacted alkanol is withdrawn from the bottom of the contacting vessel. Because the boiling points of the lower alkanols (except sec. butanol) are 10° C or more higher than the boiling point of the corresponding formates produced therefrom, the alkanol is readily removed from the reaction mixture by distillation in most instances.

The process of the invention can be carried out at a temperature of as low as 0° C and in theory could be carried out at quite high temperatures as well. However, as a practical matter, the reaction must be carried out below the temperature at which the life of the resin catalyst becomes unacceptable. A suitable range of temperature is 0°–200° C, 20°–100° C being preferred.

The overall reaction between CO and alkanols to form formates is quite highly exothermic. This, of course, means that a considerable amount of heat must be removed from the system to avoid overheating the catalyst. One preferred way of doing this is to recycle cold reaction product to the reactor to absorb heat of reaction. The alkyl formate component of the reaction product is inert and thus functions as a heat sink to keep the temperature of the reactants and the catalyst at a suitably low level. The warm reaction product can then be cooled by conventional external heat exchangers. It is preferred to recycle 5–98% and still more preferably 30–95% by weight of the reaction mixture for this purpose.

The time of contact of the reactants and catalyst required to effect the conversion depends upon a number of operating variables such as conversion level, temperature, pressure, alkanol type, production rates and the like. It is, however, necessary that the velocity of each phase through the foramina of the catalyst bed be such as to assure a residence time of at least 0.1 second and preferably 1 second within the catalyst bed. Higher conversion of alkanol to formate is favored by longer contact times with the resin catalyst and therefore residence times as large as 20–30 minutes can be used to attain extremely high conversions.

EXAMPLE I

This example illustrates the method of resin preparation which was used for the process examples which follow.

Fifty ml of A-26 macroreticular ion exchange resin were charged to a 100 ml buret in the form of an aqueous slurry. The resin was converted to the hydroxyl form with 1N NaOH by slowly introducing 250 ml of the caustic solution into the top of the buret while simultaneously withdrawing an equal volume of liquid from the tip. Following this caustic wash, the resin was washed with water to remove excess caustic. In addition, to reduce the incidence of hydrolysis of alkyl formate reaction product, the water in the buret surrounding the resin was displaced by a like amount of the lower alkanol to be used in subsequent test runs to make alkyl formates.

EXAMPLE II

A 0.5 inch O.D. stainless steel tubular reactor was charged with 40 ml of A-26 ion exchange resin prepared in the manner described in Example I. The reactor was then continuously charged simultaneously with liquid methanol at the rate of 2.0 grams per second and with gaseous CO at the rate of 1.0 cm$^3$ per second. Pressure was held at 1500 psig and temperature was maintained at 47° C. Analysis of the liquid effluent showed the presence of methyl formate in excess of 0.1% by weight.

EXAMPLE III

The reactor used in Example II was modified to provide for recirculation of the effluent stream therefrom by means of mixing with fresh feed. Methanol was introduced into the reactor at the rate of 1 g for each 30 g of recirculated effluent stream. A corresponding portion of effluent stream was removed from the system in order to maintain a constant liquid volume in the system. Analysis of the effluent product showed that it contained over 12% by weight methyl formate.

EXAMPLE IV

Three additional tests using the experimental procedure of Example III were carried out in the same manner except for the substitution of the following commercially available resins which had been treated in accordance with Example I:

IRA – 900
IRA – 900C
IRA – 910

The results were substantially the same as in Example III.

I claim:

1. A process for making lower alkyl formate comprising contacting continuously in a closed reactor having a fixed foraminous bed of resin catalyst, an intimate admixture of gaseous CO and liquid $C_{1-4}$ alkanol, said resin catalyst being a strongly basic anion exchange resin in which:
    (a) the polymer matrix of the anion exchange resin is poly(styrenedivinylbenzene) and
    (b) the ion-active group of the anion exchange resin corresponds to the structural formula $-CH_2NR_3^+$ in which the R groups are independently selected from the group consisting of $C_{1-4}$ alkyl and hydroxyl-substituted $C_{1-2}$ alkyl groups by which a reaction mixture is formed containing alkyl formate.

2. The process of claim 1 in which the alkanol is methanol.

3. The process of claim 1 in which the ion-active group is derived from trimethylamine.

4. The process of claim 1 in whih the ion-active group is derived from dimethylethanolamine.

5. The process of claim 1 in which the contacting step is carried out at 20°–100° C.

6. The process of claim 1 in which the contacting step is carried out by passing the alkanol and the CO countercurrently through the catalyst bed.

7. The process of claim 1 in which the contacting step is carried out by passing the alkanol and the CO cocurrently through the catalyst bed.

8. The process of claim 1 in which 10–50% by weight of the reaction mixture is cooled and recycled to the reactor.

9. The process of claim 8 in which the portion of the reaction mixture to be recycled is blended with alkanol and then recycled to the reactor.

* * * * *